United States Patent [19]

Anderson et al.

[11] 4,211,227

[45] Jul. 8, 1980

[54] SURGICAL SPONGE MATERIAL

[75] Inventors: Gary C. Anderson, Framingham; Jon A. Howey, Mansfield, both of Mass.; Harish A. Patel, Crystal Lake, Ill.

[73] Assignee: The Kendall Company, Boston, Mass.

[21] Appl. No.: 921,544

[22] Filed: Jul. 3, 1978

[51] Int. Cl.$^2$ .............................................. A61F 13/00
[52] U.S. Cl. ..................................... 128/296; 428/198
[58] Field of Search .......... 128/156, 284, 287, 290 W, 128/296; 428/223–224, 227, 280, 282, 286, 287, 299, 305

[56] References Cited

U.S. PATENT DOCUMENTS

| | | | |
|---|---|---|---|
| 3,345,243 | 10/1967 | Kalwaites | 128/290 W |
| 3,542,634 | 11/1970 | Such et al. | 128/156 |
| 3,695,269 | 10/1972 | Malaney | 128/284 |
| 3,695,985 | 10/1972 | Brock et al. | 428/198 |
| 3,837,338 | 9/1974 | Chesky et al. | 128/156 |
| 3,868,287 | 2/1975 | Lewyckyj | 128/284 |
| 3,934,588 | 1/1976 | Mesek et al. | 128/290 W |
| 4,093,765 | 6/1978 | Schmidt | 128/296 |

Primary Examiner—C. Fred Rosenbaum
Attorney, Agent, or Firm—Edward J. Scahill, Jr.

[57] ABSTRACT

A nonwoven hospital sponge material has been provided comprising a layered fabric having an inner core of a substantially hydrophilic material disposed adjacent at least one outer or surface layer or between a pair of outer layers of a substantially hydrophobic material, said sponge material being bonded by passing the material through rolls engraved in a pattern of lands and grooves in such a way that a repeating pattern of three degrees of compression are imposed therein: high compression, intermediate compression and, little or no compression. A nonwoven fabric bonded in this manner becomes more absorbent, loftier, has good surface integrity and does not adhere to the wound surface, when the nonwoven sponge material is then compacted subsequent to the bonding step. This thusly constructed, rather lighweight nonwoven material, produces a relatively inexpensive and disposable hospital sponge and dressing material having all of the desirable features of the more expensive woven materials commonly used today.

9 Claims, 5 Drawing Figures

SURGICAL SPONGE MATERIAL

BACKGROUND OF THE INVENTION

This invention is concerned with surgical sponges and dressings and more specifically to an inexpensive disposable primary dressing for use in a hospital that most nearly approaches the advantageous characteristics of the more expensive dressing materials.

Conventional wound dressings in the form of sponges and the like can generally be divided into four major types or categories.

Plain gauze dressings are generally transfer types of dressings used either directly on a wound or indirectly over a non-adherent dressing. The primary function of this type dressing is to lift and transfer the blood and other exudates from the wound into a fluid holding reservoir, such as an abdominal pad.

Washed gauze dressings are used where a softer, more open mesh, bulkier sponge might be needed for transfer. Such dressings have been made to provide a sponge structure that when applied, supplies some gentle pressure and cushioning than unwashed gauze sponges, however, inherently the structure is not uniform in thickness and several plies have to be utilized to provide optimal pressure.

Another type of dressing in use today is a filled gauze sponge, which consists of one or two plies of unwashed gauze, an inner matrix of cotton or rayon fibers, and in some cases a layer of creped cellulose wadding used as an inner carrier. This type of dressing can be utilized as a small fluid reservoir for soaking up and holding limited amounts of exudate. It lacks the softness and bulk, and the ability to transfer exudates in the same amounts that can be achieved with washed gauze.

Finally, another type of sponge or dressing being used today is similar to the filled gauze sponge with the only difference being the replacement of the gauze cover with a nonwoven material. Dressings of this type have characteristics similar to filled gauze sponges, but have additional deficiencies, for example, the structure has decreased strength when wet as compared to gauze, and the existence of a chemical binder in nonwoven material can be potentially irritating to some patients. Also, some of this type sponge or dressing have an apertured nonwoven cover that not only adheres to the wound, but because the apertures are larger than the granulating tissue it covers, then this tissue tends to grow through the apertures and retards healing. This type dressing has the further problem that its transfer characteristics are poor due to the cellulose wadding filler.

A disposable surgical dressing is yet to be produced inexpensively that is absorbent, but has good fluid transfer properties; will not adhere to the wound; and, has good surface integrity so as to remain as "lint free" as possible.

Accordingly, it is an object of the present invention to provide an inexpensive disposable primary dressing for hospital use that has all of the advantages of the more expensive counterparts without their inherent disadvantages.

It is another object of this invention to produce a nonwoven dressing material that has high fabric volume per unit of weight, good imbibition of liquids and good surface integrity.

It is still another object of this invention to achieve the above-described characteristics in a nonwoven material by bulking a layered, thermally bonded material.

SUMMARY OF THE INVENTION

A nonwoven surgical dressing material includes an inner core of a substantially hydrophilic fibers or blends of fibers having a substantially hydrophilic property characterizing same, said inner core being disposed adjacent to or sandwiched between outer or surface layer(s) of substantially hydrophobic fibers or blends of fibers having a substantially hydrophobic property characterising same. The thusly structured material may be bonded by passing the material through heated rolls engraved in a pattern of lands and grooves in such a way that imparts a repeating pattern thereon of three degrees of compression: high compression, intermediate compression and little or no compression. This bonded fabric is then compacted, thereby becoming bulkier, softer and more absorbent. Owing to the substantially hydrophobic nature of the outer layers of the dressing, it is also non-adherent and has good surface integrity—yet, with all these advantages, the product is relatively inexpensive to manufacture.

DESCRIPTION OF THE PREFERRED EMBODIMENTS

A unitary nonwoven fabric composed of layers of fibers is bonded together with heat and pressure, and is subsequently bulked or compacted to produce a fabric having high fabric volume per unit weight, having good imbibition of liquids, non-adherent characteristics, and has good surface integrity, as well as having improved absorbent capacity and fluid transfer rates from the outer layers to the inner core, and on to a secondary dressing.

Figure 1:
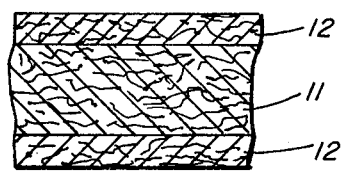
FIG. 1 is a sectional view of the layered structure of this invention prior to bonding and compacting.

Referring to the drawings, FIG. 1 shows such a layered fabric wherein an inner layer of substantially hydrophilic textile-length fibers 11 has at least one outer layer 12 of substantially hydrophobic textile-length fibers in bonded contact therewith. The layers are bonded together with heat and pressure by passing the array between a pair of rolls which are both engraved in a pattern of lands and grooves which forms a series or pattern of pressure areas of various degrees. In general, the overall character of the fiber-displacement pattern caused by the bonding can be shown in FIG. 2 wherein three bonding areas are disclosed: a highly compacted area 22 where a land on one roller has traversed a land on another roll; an intermediately compressed area 23 formed where a land on one roll has traversed a groove on the other roll; and, a substantially uncompacted area 24 where a groove on one roll has traversed a groove on the other roll. There are approximately 25% highly compacted areas, 25% uncompacted areas and 50% intermediately compacted areas in any modular position of the bonded fabric, and the areas are in the form of quadrilaterals with parallel but do not necessarily have equal sides, herein given the term rhomboidal. Such a bonding process is outlined and described in U.S. Pat. No. 3,542,634, of common assignee.

While FIG. 1 shows an inner layer of substantially hydrophilic fibers sandwiched between a pair of outer layers of substantially hydrophobic fibers, it should be understood that a single outer surface can be successfully used herein. Further, such a construction could be folded over on itself forming essentially the same fabric as shown in FIG. 1. Thus, we are actually disclosing a nonwoven fabric having an inner layer of substantially hydrophilic textile-length fibers, and at least one outer or surface layer of substantially hydrophobic textile-length fibers.

Figure 2:
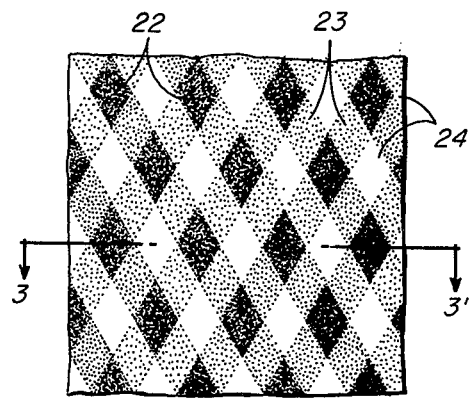
FIG. 2 is a plan view of the fabric shown in FIG. 1, and shows the degrees of compression used in the bonding step.
Figure 3:
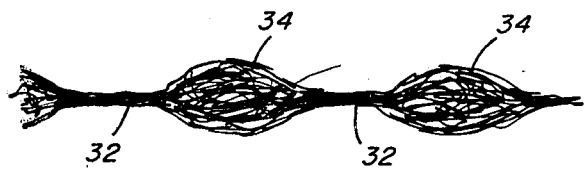
FIG. 3 is a sectional view of the fabric in this invention after bonding has occurred.

FIG. 3 is a sectional view of the bonded fabric of FIG. 2 wherein the high compacted areas 32 have nearly no open or porous areas therein due to the high compaction and fusion of fibers therein. The substantially uncompacted areas 34 can be seen to be relatively porous and open due to the lack of compaction (groove to groove traverse) therein.

The thusly bonded fabric is then compacted or bulked by treating, for example, with apparatus such as is described in U.S. Pat. No. 3,260,778, or the like. Micro-pleats or the like can be imparted to a fabric by squeezing or compacting same, which compaction causes the fabric to become rearranged into a repeating series of wave-like undulations substantially throughout its length and running across the width of the fabric.

Upon compaction or bulking, the rhomboidal areas of varying compression become more open and porous due to the fiber rearrangement and displacement taking place therein. This would be especially true of the intermediately compressed and the uncompressed areas, which comprise approximately 75% of the area of the fabric. The stresses produced in a compaction process have a greater rearranging effect on these areas. This characteristic is what makes it possible for the fabric to be bulked without seriously breaking the major bonds holding the fabric together. The absorbent capacity of the thusly treated fabric is increased nearly two fold. Furthermore, due to increased surface area, wicking and fluid transfer rates are also advantageously increased.

Figure 4:
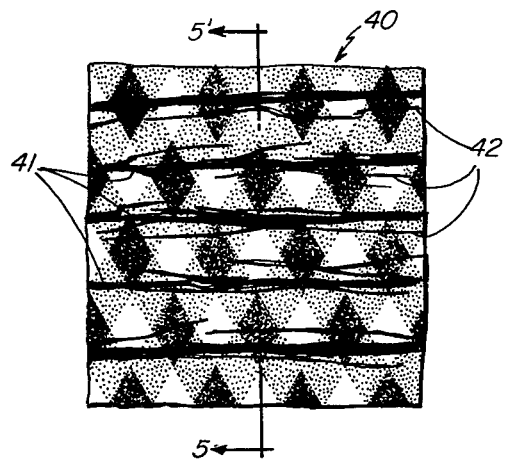
FIG. 4 is a plan view of the fabric of this invention after the bonding and compacting steps have been taken.
Figure 5:
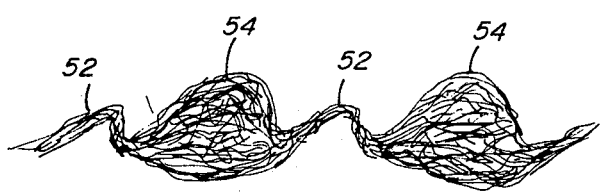
FIG. 5 is a sectional view of the bonded fabric of this invention after the compacting step has been performed.

FIG. 4 shows a fabric 40 that has been bonded and compacted as described herein, wherein wave-like undulations, such as 41, are imparted into the fabric. Slightly lesser undulations or micro-pleats 42 are also interspersed generally throughout the fabric. It has been found that these undulations 41 and 42 are able to open up the interfiber relationships therein without seriously breaking the major bonds holding the fabric together. FIG. 5 further shows this especially when compared to FIG. 3. In FIG. 5, the highly compacted or bonded areas 52 can be seen to be somewhat more porous and open than before the compacting step was performed; while the intermediately compacted areas (not shown) and the substantially uncompacted areas 54 are much more open and porous, thereby permitting the fabric to be substantially more absorbent and have more loft than its untreated counterpart, while still maintaining the major fabric bonding mechanism.

A primary dressing for hospital use can be made from this material that has all of the advantages of the more expensive counterparts without their inherent disadvantages. For example, using polyester fibers with a hydrophilic finish (such as 1.5 denier, 1½" Eastman Type 41D) in the outer layers sandwiched around, for example, a predominately rayon inner core layer produces a surgical dressing having the following qualities or attributes important to such a dressing: excellent nonadherence characteristics; absorbent qualities found in the more expensive conventional dressings; and, surface integrity, or the lint-free characteristic, is improved significantly.

The following examples are illustrative of the fabrics of this invention:

EXAMPLE I

An array of fiber layers comprising a pair of outer or surface layers of 100% 1.5 denier, approximately 1½" polyester fibers, each being approximately 20% of the total fabric weight (gms/sq. yd.), sandwiched around blended inner core layer of 85% 1.5 denier 1 9/16" rayon fibers and 15% 3.0 denier, 1½" polyester binder fibers, said inner layer being approximately 50% of the total fabric weight and being bonded with heat and pressure generally as outlined in U.S. Pat. No. 3,542,634. The repeating pattern of the variously compacted rhomboidal areas is thereby formed thereon.

This thusly layered fabric is then treated with a compactor, such as is described in U.S. Pat. No. 3,260,778 or the like, so as to impart a repeating series of wave-like undulations substantially throughout its length and width and to cause portions of the highly compacted areas, the intermediately compacted areas and the substantially uncompacted areas to become more open and porous than before said treatment.

The resulting fabric weighs approximately 37.6 gms/sq. yd., has a thickness of 26.0 mils (as measured by the Ames-Mercer gauge), a bulk of 14.7 cm$^3$/gm. and an absorbent capacity of approximately 1100%. These figures compare favorably with those of the same fabric prior to being compacted: 34 gm/sq. yd., a thickness of 12.5 mils, a bulk of 7.85 cm 3/g and an absorbent capacity of 640%.

EXAMPLE II

An array of fiber layers comprising a pair of outer or surface layers of 80% 1.8 denier 1½" polypropylene fibers and 20% 3.0 denier polyolefin binder fibers sandwiched around an inner core layer of 75% of bleached comber cotton and 25% of the 3.0 denier polyolefin binder fiber. The fabric is bonded and compacted as described in Example I.

The resulting nonwoven fabric was a soft, absorbent material having good surface integrity and similarly favorable improvements in bulk, thickness and absorbency as described above in Example I.

EXAMPLE III

Another method of making a nonwoven fabric for use as a primary surgical dressing, or the like, is to make a two-layered structure in the same manner as described above, wherein the first layer is approximately 6 grams/sq. yd. of 1½" 1.5 denier polyester fibers and a second layer of approximately 24 grams/sq. yd. composed of 80% 1 9/16" 1.5 denier rayon fibers and 20% 1½" 3.0 denier polyester binder fibers. This two-layered structure is bonded with heat and pressure between the engraved rolls described in Example I. The fabric is then compacted as described earlier in Example I. This bonded and compacted fabric is then folded over on itself in a manner such that the rayon layer becomes the inner layer sandwiched between the polyester outer layers.

This resulting nonwoven primary dressing material will have as improved an absorbent capacity as the 3-ply structure. The fabric has the desired nonadherence characteristics and the absorbent qualities of conventional dressings, while the surface lint present thereon has been significantly reduced.

As can be observed above, the absorbent capacity of the fabrics have been significantly and unexpectedly increased due to the compacting step. Whereas the fabrics, such as outlined above, have an absorbent capacity before compacting of about six times its own weight, the same fabrics increase their absorbent capacity to more than eleven times their own weight after compaction, while still maintaining a good fiber bond therein.

Substantially hydrophobic and thermoplastic outer layers and substantially hydrophilic inner layers used in this invention unexpectedly provides the fabrics produced herein with a combination of useful properties, as compared to the products shown in the examples of U.S. Pat. No. 3,542,634. For instance, Example I of U.S. Pat. No. 3,542,634 has surfaces of all cotton as opposed to the substantially hydrophobic surface used herein, and even though the patent states that fabrics described therein are "lint free" it is urged that the fabrics described in this invention, having substantially thermoplastic and hydrophobic surfaces is much more lint free than one with a cotton surface, partially due to fusion of the thermoplastic fibers used herein. Cellulosic fibers form only weak self bonds with adjacent cellulosic fibers in a heat and pressure bonding process, such as is used herein, and these bonds are usually destroyed by aqueous liquids. Additionally, cellulosic fibers are somewhat brittle and the carding action used to produce nonwoven webs tends to break some fibers and results in the undesirable presence of short fiber lint or dust. However, thermoplastic fibers are more resilient, by their nature, and are less prone to breakage. Furthermore, thermoplastic fibers will form bonds with adjacent fibers in such a heat and pressure bonding operation as is used herein, and these bonds are not destroyed by aqueous liquids, thereby increasing the surface integrity of the fabric.

In order to more accurately describe this invention, the hydrophobic property of the outer or surface layer should have a rather high degree of hydrophobicity. The degree of hydrophobicity is commonly reported as the percent moisture regain for fibers, at 70° F. and 65% relative humidity. For the purposes of this invention, the fibers used in the hydrophobic layers, should have a moisture regain of less than 5%.

The outer surface of substantially thermoplastic fibers and inner layer of substantially hydrophilic fibers also has the additional features of good absorbency with the correspondingly desirable feature of nonadherence. These features are especially good properties for a primary hospital dressing. Having the hydrophobic surface in close contact with the wound permits the ready transfer of body fluids into secondary dressings, but it will not adhere to the wound itself. The hydrophobic surface will only transfer body fluids but will not retain moisture while the hydrophilic layer or surface will collect that body fluid and will also transfer the fluid into an adjacent secondary dressing.

Of course, in addition to the use of this fabric as a primary dressing or surgical sponge material, it is urged that the material could also be advantageously used as dressing substrate for finger bandages, or the like.

Since it is obvious that many modifications and embodiments can be made in the above-described invention without changing the spirit and scope of the invention, it is intended that this invention not be limited by anything other than the appended claims.

What is claimed is:

1. A nonwoven fabric comprising:
   an inner layer of substantially hydrophilic textile-length fibers; and,
   outer layers of substantially hydrophobic textile-length fibers disposed on both sides of said inner layer;
   said inner layer and said outer layers being bonded together at a set of discrete and spaced apart rhomboidal highly compacted areas, each of said highly compacted areas being fully bounded on each of its four sides by a rhomboidal area of intermediately compacted fibers, and each of said highly compacted areas being contiguous at each of its four apices with a rhomboidal area of substantially uncompacted fibers;
   said thusly bonded fabric further arranged in a repeating series of wave-like undulations substantially throughout its length, said indulations running across the width of the fabric and causing major portions of said intermediately compacted areas and said substantially uncompacted areas, and minor portions of said highly compacted areas, to become more open and porous by opening the interfiber relationships therein without substantially breaking said rhomboidal compacted areas.

2. The nonwoven fabric of claim 1 wherein said inner layer of substantially hydrophilic fibers is a blend of 55-100% rayon fibers and 45-0% polyester fibers.

3. The nonwoven fabric of claim 1 wherein said outer layers of substantially hydrophobic fibers are of polyester fibers.

4. The nonwoven fabric of claim 1 wherein said hydrophobic fibers in said outer layers have a hydrophilic finish thereon.

5. A surgical sponge comprising:
   an inner layer of substantially hydrophilic textile-length fibers; and,
   outer layers of substantially hydrophobic textile-length fibers disposed on both sides of said inner layer;
   said inner layer and said outer layers being bonded together at a set of discrete and spaced apart rhomboidal highly compacted areas, each of said highly compacted areas being fully bounded on each of its four sides by a rhomboidal area of intermediately compacted fibers, and each of said highly compacted areas being contiguous at each of its four apices with a rhomboidal area of substantially uncompacted fibers;
   said thusly bonded fabric further arranged in a repeating series of wave-like undulations substantially throughout its length, said undulations running across the width of the fabric and causing major portions of said intermediately compacted areas and said substantially uncompacted areas, and minor portions of said highly compacted areas, to become more open and porous by opening the interfiber relationships therein without substantially breaking said rhomboidal compacted areas.

6. The surgical sponge of claim 5 wherein said inner layer of substantially hydrophilic fibers is a blend of 55–100% rayon fibers and 45–0% polyester fibers.

7. The surgical sponge of claim 5 wherein said outer layers of substantially hydrophobic fibers are of polyester fibers.

8. The surgical sponge of claim 5 wherein said hydrophobic fibers in said outer layers have a hydrophilic finish thereon.

9. The surgical sponge of claim 7 wherein said hydrophobic fibers in said outer layers have a hydrophilic finish thereon.

* * * * *